(12) United States Patent
Xu et al.

(10) Patent No.: US 8,288,112 B2
(45) Date of Patent: Oct. 16, 2012

(54) PROTEIN, AN ANTIBODY AND MEASUREMENT OF THE PROTEIN

(75) Inventors: Shengyuan Xu, Uppsala (SE); Per Venge, Uppsala (SE)

(73) Assignee: P&M Venge AB, Uppsala (SE)

( * ) Notice: Subject to any disclaimer, the term of this patent is extended or adjusted under 35 U.S.C. 154(b) by 671 days.

(21) Appl. No.: 12/298,161

(22) PCT Filed: Apr. 20, 2007

(86) PCT No.: PCT/SE2007/000377
§ 371 (c)(1),
(2), (4) Date: Oct. 23, 2008

(87) PCT Pub. No.: WO2007/123462
PCT Pub. Date: Nov. 1, 2007

(65) Prior Publication Data
US 2009/0233316 A1    Sep. 17, 2009

Related U.S. Application Data

(60) Provisional application No. 60/794,898, filed on Apr. 25, 2006.

(51) Int. Cl.
*G01N 33/53* (2006.01)
(52) U.S. Cl. .......................... 435/7.1; 436/518
(58) Field of Classification Search .................. None
See application file for complete search history.

(56) References Cited

U.S. PATENT DOCUMENTS

2005/0196852 A1   9/2005  Jones et al.
2007/0015271 A1*  1/2007  Rosen et al. .............. 435/252.1

FOREIGN PATENT DOCUMENTS

WO    WO 0222660    *  3/2002

OTHER PUBLICATIONS

Mackay et al., Genetics 2003, vol. 163, p. 1365-1375.*
Ota et al., Nat. Genet. 36:40-45(2004).*
Kuno et al., J Biol. Chem 1993, vol. 268, p. 13510-13518.*
Ashmun et al., Blood 1992, vol. 79, p. 3344-3349.*
Molecular Biology of Gene 4th edition, Jane Reece Gillen editor, 4th edition, 1988, p. 342, p. 343, p. 442, and p. 445.*
Green et al., Pro. Natl. Acad. Sci. 1999, vol. 96, p. 4176-4179.*
Erlenbach et al., J. Biol. Chem 2001, vol. 276, p. 29382-29392.*
Noutoshi et al., Plant Journal 2005, vol. 43, p. 873-888.*
Bowie et al., Science, 1990, vol. 247:1306-1310.*
Morgan, Clive P. et al, "Identification of phospholipase B from *Dictyostelium discoideum* reveals a new lipase family present in mammals, flies and nematodes, but not yeast", Biochem. J, 2004, vol. 382, 441-449.
Maury, Eric et al, "Human epidermis is a novel site of phospholipase B expression", Biochemical and Biophysical Research Communications, 2002, vol. 295, 362-369.
Wang, Aijun et al, "Mammalian lysophospholipases", Biochimica et Biophysica Acta, 1999, vol. 1439, 1-16.
Database Uniprot No. Q6P4A8, Jul. 5, 2004, (version 1), Aug. 21, 2007 (version 21).

* cited by examiner

*Primary Examiner* — Jacob Cheu
(74) *Attorney, Agent, or Firm* — Porter Wright Morris & Arthur

(57) ABSTRACT

A novel mammalian protein related to human hypothetical protein FLJ22662 (SEQ ID NO: 1) and homologous hypothetical proteins from mammal species other than *Homo sapiens*. The protein is expressed in neutrophils and is characterized as a phospholipase B of a novel family (PLB-II). The protein is characterized in comprising one or two single chain polypeptide SU subunits that are different with respect to their amino acid sequences (i.e. at least one SU1 subunit and/or at least one SU2 subunit), where the amino acid sequence of: i) SU1 comprises SEQ ID NO: 2 or a variant thereof ii) SU2 comprises SEQ ID NO: 3 or a variant thereof. There is also described an antibody preparation which is specifically directed against the mammalian protein and a method for determining the occurrence or level of an analyte in a sample. The method is characterized in that analyte is related to the mammalian protein.

36 Claims, No Drawings

PROTEIN, AN ANTIBODY AND MEASUREMENT OF THE PROTEIN

RELATED APPLICATION

This application is a 371 of PCT/SE2007/000377 filed Apr. 20, 2007 and claims priority under 35 U.S.C. 119 of U.S. application Ser. No. 60/794,898 filed Apr. 25, 2006.

TECHNICAL FIELD

The present invention relates to a novel kind of protein and its subunits. The protein, in particular a subunit thereof, is enzymatically active typically by exhibiting phospholipase B activity or by being a pro-phospholipase B (i.e. are PLBs). The protein, its DNA and its activation route are different from the PLBs so far recognized. It has therefore been named PLB-II (the human variant HPLB-II) in order to distinguish it from previously known PLBs. The human variant is related to human hypothetical protein FLJ22662 (SEQ ID NO: 1).

BACKGROUND ART

The neutrophil plays an important role in both innate immunity and in inflammatory reactions in human disease (Burg et al., *Clin. Immunol.* 99, 7-17 (2001)). The neutrophil eliminates invading microorganisms through phagocytosis, generation of reactive oxygen metabolites and release of microbicidal substances stored in different granules in neutrophil. Apart from secretory vesicles, neutrophils contain azurophil, specific (secondary) and gelatinase-containing granules (tertiary) (Borregaard et al., *Blood* 89, 3503-3521 (1997)) formed in the bone marrow at subsequent stages of neutrophil maturation (Borregaard et al., *Blood* 85, No 3, 812-817 (1995)). During neutrophil-mediated inflammatory reactions the secretory vesicles are mobilized first upon stimulation, followed by the tertiary, the secondary and the azurophil granules (Sengelov et al., *J. Immunol.* 154, 4157-4165 (1995); and Sengelby et al. *J. Immunol.* 150 No. 4, 1535-1543 (1993)). Upon phagocytosis, the azurophil granules fuse with the phagosomes, which causes the release of proteolytic and bactericidal factors into the phagolysosome, where the invading microorganism is killed and digested (Burg et al., (2001) cited above).

Phospholipase Bs (Ghannoum et al., *Clin. Microbiol. Rev.* 13, 122-43, Table (2000)) are a heterogeneous group of enzymes that can hydrolyze both the sn-1 and sn-2 fatty acids of glycerophospholipids, and thus display both phospholipase $A_1$ or phospholipase $A_2$ and lysophospholipase activities. Several PLBs have been identified in various microorganisms (Ghannoum et al., (2000) cited above; and (Farn et al., *J. Bacteriol.* 183, 6717-6720 (2001)), fungi (Ghannoum et al., (2000) cited above), *Dictystelium discoideum* (Ferber et al., *Eur. J. Biochem.* 14, 253-257 (1970)) and in the brush border membrane of mature enterocytes from guinea pig (Gassama-Diagne et al., *J. Biol. Chem.* 267, 13418-13424 (1992)), rat (Tojo et al., *J. Biol. Chem.* 273, 2214-2221 (1998), rabbit (Boll et al., *J. Biol. Chem.* 268, 12901-12911 (1993)) and human epidermis (Maury at al., *Biochem. Biophys. Res. Commun.* 295, 362-369 (2002)). PLBs are also important components of venoms from bees and snakes. Bacterial and fungal PLBs have been reported to be virulence factors that damage host cells, while PLBs of enterocytes from mammals are involved in digestion of dietary lipids, and PLB expressed in human epidermis probably plays a role in the differentiation process and is involved in the epidermal barrier function.

The full length of the FLJ22662 protein comprises 552 amino acid residues (SEQ ID NO: 1, AAH63561). A recombinantly produced FLJ22662 protein containing a sequence of 223 residues from the full length variant (a.a 330-552) (AAH00909, Strausberg et al., Proc. Natl. Acad. Sci. U.S.A. 99 (26), 16899-16903 (2002)) fused to GST is commercially available from Novus Biologicals (Littleton Colo., US). Suggested uses are Western blot, ELISA, and assay development. US patent applications 20070059717, 20070004038, 20060252056, 20060240426, 20060199204, 20060194199, 20060111314, 20060073496, 20060046259, 20060019256, 20050208500, 20050095607, 20040076955, 20040005563, 20030170743, and 20030165949 (issued as U.S. Pat. No. 7,189,507) are related to the diagnosis and therapy of various diseases and mention FLJ22662 proteins and their genes as one out of many other proteins that might be of interest.

All US patents and patent applications including published International patent applications designating the US are hereby incorporated in their entirety into the present specification.

OBJECTIVES

The identification and characterization of novel granule proteins in human neutrophils is an important approach to study the functions of human neutrophils. In searching for novel granule proteins, we found a protein of molecular weight 130 kDa in acid extracts of granulocytes containing 25 and 45 kDa subunits/molecules. The amino acid analysis identified this protein as a product of a gene (FLS22662) which encodes a protein of 63 kDa with unknown function. Comparison of this protein with the GenBank sequence database using the BLAST program revealed an amino acid sequence similarity with *Dictyostelium* phospholipase B (PLB), suggesting a putative PLB. The objectives of the invention comprise:

1. Understanding of the biological significance in health and disease of the novel protein.
2. Development of new drug principles based on the found activity of the protein as such including its individual subunits, e.g. PLB-II activity. This could be accomplished by:
   a) using the protein as such or its individual subunits either in native or in recombinant form, or b) mimicking the activity of the novel protein or its subunits for the design of new drug principles, or c) the development of principles that facilitates the conversion of proforms into active forms.

This approach should prove valuable in the design of new antibiotic drugs, but could also prove valuable as an anti-thrombotic principle in other situations where the activity is physiologically important.
3. Development of inhibitory principles for the activity, e.g. PLB-II activity. This could be accomplished by a) development of drugs that inhibit the activity, or b) drug principles that prevent the transformation of pro-forms into active forms.

The inhibition of activity should prove valuable in a large number of human diseases such as inflammatory disease, cardiovascular disease, lipid disorders in which neutrophil granulocytes and monocytes/macrophages are known to be involved etc.
4. Development of sensitive assays for the measurement of the activity of the protein and/or its individual subunits either alone or in combination. The assay principles may be based on: a) immunological principles including also other affinity principles between forms of our novel protein and a non-immunological affinity counterpart, b) the measurement of the enzymic activity, and/or c) detection of mRNA expression of the gene that relates to the protein (FLJ22662 in humans). This objective includes diagnostic methods in which the level of the novel protein, its individual subunits and/or mRNA expression in a body fluid or other tissue is/are deviating from the corresponding levels of healthy individuals and a used as a marker for diseases and other physiological conditions that are related to deviating levels of these biological entities.

THE INVENTION

The invention comprises three main aspects: 1) A mammalian protein that comprises one or more subunits each of which is related to a fragment of hypothetical human protein FLJ22662 or to corresponding fragments in the homologous hypothetical proteins from mammalian species other than *Homo sapiens*. There may possibly also be other subunits in the protein of the invention. 2) An antibody preparation specific for the mammalian protein defined in this specification. 3. A method for measuring the occurrence of an analyte in a sample. The analyte is related to the mammalian protein of the first main aspect.

A Novel Mammalian Protein (First Main Aspect)

This aspect relates to a mammalian protein that is characterized in being derived from a) hypothetical human single chain protein FLJ22662 which exhibits the amino acid sequence of SEQ ID NO: 1 and in gelfiltration and possibly also in vivo is present as a protein containing four non-covalently associated single chain polypeptide subunits (SU subunits) that pair-wise are different non-overlapping fragments (two SU1 subunits and two SU2 subunits) of SEQ ID NO: 1, and/or b) a homologous hypothetical protein of a mammalian species other than *Homo sapiens*, which in a similar manner as FLJ22662 is capable of giving fragments that can associate with each other to give a multimeric protein containing SU1 and SU2 subunits which are homologous to the subunits/fragments deriving from the FLJ22662 protein.

The term "hypothetical protein" will in the context of the invention mean a single chain protein that like FLJ22662 can be isolated from biological material as a native multimeric protein containing at least two non-covalently associated single chain polypeptide subunits (SU1 and SU2 subunits) that correspond to different non-overlapping fragments of the hypothetical protein. The in vivo occurrence of this kind of hypothetical proteins is often too low or too rare to be measured and/or detected. The sequence of the SU1 subunit is typically located closer to the amino-terminal end of the hypothetical protein than the sequence of the SU2 subunit.

The mammalian protein of the invention is further characterized in comprising an SU1 subunit and/or an SU2 subunit. One or both of the different subunits may be present in the protein as a duplicate, a triplicate etc and/or there may be one or more additional subunits of other kind(s). The SU1 subunits and/or the SU2 subunits may derive from the same or from different species (man-made forms). Individual SU subunits may also be chemically derivatized forms and/or recombinant forms including mutated forms that do not exactly correspond to SU subunits of any particular mammalian species.

The SU1 subunit comprises SEQ ID NO: 2 or a variant thereof which is obtained by substitution, deletion and/or addition of one or more amino acid residues in SEQ ID NO: 2. The SU2 subunit comprises SEQ ID NO: 3 or a variant thereof which is obtained by substitution, deletion or addition of one or more amino acid residues in SEQ ID NO: 3. The term "variant" includes that the sequence of an SU variant exhibit a sequence identity of $\geq 50\%$, such as $\geq 60\%$ or $\geq 75\%$ or $\geq 80\%$ or $\geq 90\%$ or $\geq 95\%$ with the subunit it is a variant of, i.e. SEQ ID NO: 2 or SEQ ID NO: 3. The ranges include that sequences/subunits/fragments may derive from homologous proteins of different species as well as variants obtained by genetic engineering. The term "sequence identity" refers to the program used in the experimental part to determine sequence identity. SEQ ID NO: 2 and SEQ ID NO: 3 occur as non-overlapping regions in SEQ ID NO: 1 with SEQ ID NO: 2 being located closer to the amino-terminal end of SEQ ID NO: 1 than SEQ ID NO: 3.

The substitution, deletion and/or addition of residues shall preferably not extinguish all important biological functions of native forms of the subunits and/or the corresponding multimeric protein. Their capability of associating to each other or to exhibit enzyme activity, such as PLB-II or pro-PLB-II activities, should at least be partially retained, for instance.

In one variant a part of a specified length of the sequence in an SU subunit is identical to a part of the same length A) in the sequence of hypothetical FLJ22662 protein and/or B) in the sequence of a corresponding homologous hypothetical protein of a mammalian species other than *Homo sapiens*.

A) In a subvariant an SU1 subunit and/or an SU2 subunit comprise at least one, two or more amino acid sequences of $\geq 5$, such as $\geq 10$ or $\geq 15 \geq 25$ or $\geq 50$ amino acid residues which sequences are present in SEQ ID NO: 1 or in corresponding parts of the sequence of a homologous hypothetical single chain protein of a mammalian species other than *Homo sapiens*.

B) In another subvariant,
  a) an SU1 subunit comprises at least one, two or more amino acid sequences of $\geq 5$, such as $\geq 10$ or $\geq 15 \geq 25$ or $\geq 50$ amino acid residues which sequences are present in SEQ ID NO: 2 or in corresponding parts of the sequence of a homologous hypothetical single chain protein of a mammalian species other than *Homo sapiens*, and/or
  b) an SU2 subunit comprises at least one, two or more amino acid sequences of $\geq 5$, such as $\geq 10$ or $\geq 15 \geq 25$ or $\geq 50$ amino acid residues which sequences are present in SEQ ID NO: 3 or in corresponding parts of the sequence of a homologous hypothetical single chain protein of a mammalian species other than *Homo sapiens*.

This kind of part sequence in an SU1 subunit should be non-retrievable in an SU2 subunit and vice versa for an SU2 subunit.

The molecular weight $M_w$ of the mammalian protein of the invention depends on the number and kinds of SU subunits in it as well as on the species origin of the subunits and on particular deletions, substitutions or additions of amino acid residues. Typical $M_w$s are within the range of 15-240 kDa presuming the number of subunits is 1-4. For single SU1 subunits the typical range is 15-35 kDa and for single SU2 subunits 30-60 kDa. For variants that comprise four subunits the typical range is 60-240 kDa with a more narrow range being applicable to variants in which there are two SU1 and two SU2 subunits, e.g. 90-190 kDa, such as 110-150 kDa. The $M_w$s of pure human variants are presented in the "Experimental part". These $M_w$ ranges primarily apply to the polypeptide chain(s) of the protein and subunits of the invention. They do not include the $M_w$ of groups that have been added by recombinant fusion with other proteins or by chemical derivation to attach other large molecular weight entities. The ranges given above in particular refer to $M_w$s obtained by gel filtration for multimeric proteins and by SDS-PAGE under denaturing conditions for individual subunits.

In preferred variants the protein of the invention is a lipase, such as phospholipase and most typical a phospholipase B. This includes that the protein is an active enzyme or is a pro-enzyme that is possible to transform/activate to an active enzyme, e.g. to a phospholipase B. In order for the protein to be a pro-enzyme or an active enzyme (PLB-II), it seems imperative that the novel protein has at least an SU2 subunit and optionally is devoid of the SU1 subunit. It is likely that some kind of degradation of the SU2 subunit is necessary for enzyme activity, for instance by cleaving off parts corresponding to a reduction in molecular weight of the SU2 subunit. The reduction in $M_w$ for activation is typically $\geq 0.5$ kDa, such as $\geq 1$ kDa or $\geq 2$ kDa or $\geq 3$ kDa but presumed to be $\leq 10$ kDa. Alternatively the reduction in $M_w$ may be measured in percentage, e.g. $\geq 1\%$, such as $\geq 2\%$ or $\geq 4\%$ or $\geq 6\%$ but presumed to be $\leq 20\%$ of the Mw of the subunit concerned, e.g. an SU2 subunit. Based on results so far obtained the reduction is typically $\leq 5$ kDa or $\leq 10\%$ for human variants and the like.

The amino acid sequence of the various SU subunits are lacking the lipase consensus sequence, i.e. a sequence of five amino acid residues starting and ending with glycine and having serine in the middle and independently any kind of amino acid residues at the two remaining positions (Schrag et al., *Methods Enzymol.* 284:85-107, 85-107 (1997)).

The mammalian protein of the invention may be in derivatized form where three important variants are 1) labelled forms, 2) immobilized or immobilizable forms, and 3) fused forms, i.e. recombinant forms in which one or more other compounds exhibiting polypeptide structure has been fused to one or more subunits of the novel protein.

The mammalian protein in labelled form is typically a conjugate between the protein and an analytically detectable group. Detectable groups/labels are mainly of two kinds 1) signal-generating labels, and 2) affinity labels. Typical examples of the first kind of labels are fluorophors, luminophors, such as bioluminophors and chemiluminophors, radioactive groups, enzymatically active groups, such as enzymes as such, substrates, co-substrates, inhibitors, enhancers, promoters, cofactors, coenzymes etc, particles, e.g. metal particles such as gold particles, etc. Typical examples of the second kind of labels are a member in a bioaffinity pair, such as biotin and avidin/streptavidin/neutravidin etc, hapten/antigen and anti-hapten/antigen antibodies, complementary nucleic acids, constant region of an antibody and anti-constant region antibody (naturally occurring conjugate) or microbial Ig binding proteins (protein A, G etc) etc. The techniques for producing these kinds of conjugates are well-known in the field and typically involve chemical coupling of the label to the protein of the novel mammalian protein, or, as an alternative if the label exhibits polypeptide structure, recombinant fusion of the label to the appropriate subunit(s) of the mammalian protein of the invention.

In immobilized or immobilizable forms the mammalian protein is attached to a solid phase or is capable of being attached to such a phase by exhibiting a suitable functional group that matches a "counter-group" on the solid phase.

Solid phases are well known in the field and encompass surfaces, such as inner surfaces of inner walls of reaction vessels, particles, for instance in the form of beads, which may be porous or non-porous, porous monolithic plugs, membranes, sheets etc. Beads may be in suspended form (expanded beds, stirred suspension etc) or in the form of packed beds/sedimented beds. The material in the solid phase, e.g. in particles, is typically polymeric, for instance a synthetic polymer or a biopolymer and includes also inorganic polymers such as glasses. The term biopolymer includes semi-synthetic polymers comprising a polymer chain derived from a native biopolymer. The particles and other forms of solid phases (e.g. particles packed to a bed) are typically hydrophilic in the sense that they will be saturated by water by the action of capillarity (self-suction) if in contact with an excess of water. The term also indicates that the surfaces of the solid phase material shall expose a plurality of polar functional groups each of which comprises a heteroatom selected amongst oxygen, sulphur, and nitrogen. Appropriate functional groups can be selected amongst hydroxy groups, straight ethylene oxide groups ($[-CH_2CH_2O-]_n$, where n is an integer>0), amino groups, carboxy groups, sulphone groups etc, for instance, with preference for those groups that are uncharged independent of pH. Hydrophobic solid phase materials, e.g. in the form of particles, may be hydrophilized, typically by introducing hydrophilic groups on their surface, for instance by coating.

The techniques for immobilization may be selected amongst those that are known in the field, for instance via covalent bonds, affinity bonds (for instance biospecific affinity bonds), physical adsorption (mainly hydrophobic interaction) etc. Examples of biospecific affinity bonds that can be used are bonds between avidin/streptavidin/neutravidin etc and a biotinylated affinity reactant, high affinity antibody and a haptenylated affinity reactant etc.

The mammalian protein of the present invention is in isolated form (=enriched form). This typically means that the protein is present in a purity that corresponds to an enrichment relative to its concentration in an acidic extract of granules of granulocytes of the same species origin as the protein, and in particular relative to the total concentration of proteins in such an extract. The acidic extract is of the same kind as the one used as starting material for our purification of the innovative protein. See the experimental part. Typical enrichment factors are $\geq 10$, such $\geq 10^2$ or $\geq 10^3$ or $\geq 10^4$.

The protein may be present in compositions that are in liquid or dry form, such as in spray-dried, air-dried or lyophilized form. The compositions may contain buffers and/or stabilizing agents selected from various compounds exhibiting carbohydrate structure or other polyhydroxy structures, e.g. selected among sugar alcohols, mono- and disaccharides, oligosaccharides, polysaccharides. Specific examples are glucose, saccharose, lactose, trehalose, dextran etc. Potentially interesting substances to be incorporated into compositions that are to be handled in dry form are substances that in dried form are capable of existing in a glassy state.

The mammalian protein of the invention can be obtained from native material by working up acid extracts obtained from granules of granulocytes. See the experimental part. In the future it is likely and probably will also be preferred to obtain at least the polypeptide chains of the subunits of the mammalian protein of the invention by first producing recombinantly the hypothetical single chain protein, such as FLJ22662, followed by enzymatic fragmentation, possibly by carrying out the appropriate folding and/or subunit association prior or subsequent to the fragmentation. Alternatively each kind of SU subunits is produced separately whereafter folding and subunit association are allowed to proceed. Still another alternative is to employ solid phase synthesis for the different subunits which subsequently are folded and associated to form a multimeric form of the innovative protein.

Antibodies Specific for the Protein of the Invention (Second Main Aspect).

This aspect encompasses an antibody preparation (=composition) which is specifically directed against a mammalian protein as defined for the first aspect. The specificity is for one or more different epitopes on the mammalian protein that are unique for the protein. The term "unique" in this context implicates that the epitopes are not occurring disturbingly in other molecules that are present together with the mammalian protein, for instance in vivo, or when the antibody preparation is to be used in assaying methods comprising complex formation between the mammalian protein and an affinity counter part as discussed for the third aspect of the invention.

The antibody preparation may be specific for one or more epitopes on a) an SU1 subunit or b) an SU2 subunit or c) a multimeric form of the novel protein. Alternative c) encompasses specificity for epitopes that are unique for the multimeric form and/or for SU1 and/or SU2 epitopes that are exposed on the multimeric form.

The antibody preparation of the invention is polyclonal or monoclonal and may include a mixture of different monoclonals, e.g. two or more and typically $\leq 10$.

The term "antibody" includes full length antibodies, antigen-binding fragments and chemical derivatives and various recombinantly produced forms, such as single-chain antibodies, fused forms, chimeric forms etc. In its most general meaning the term also encompasses any man-made construct that can be obtained in a form that exhibits specific affinity towards a protein of the invention, e.g. affibodies. Individual antibody active entities (e.g. capable of binding to the epitopes discussed above) in the antibody preparations of the invention may be derivatized in the same manner as outlined for the mammalian protein of the invention, e.g. the same kinds of labels and solid phases as discussed for the first main aspect may be attached to the entities.

Methods Involving Measurement of the Mammalian Protein (Third Main Aspect)

This aspect is a method for determining the occurrence or level of an analyte in a sample. The characteristic feature is that the analyte is related to the mammalian protein defined in this specification. The analyte may thus be a) the mammalian protein as such, b) an inhibitor or enhancer of the activity of the mammalian protein, c) an inhibitor or enhancer of the transformation of a proform of an enzyme active form of the mammalian protein to an active form exhibiting at least a higher activity than the proform, etc. Alternative c) that the enhancer may be an enzyme that promotes the conversion into the active form of the mammalian protein or an enhancer for such an enzyme. Alternative b) and c) include also determining the capability of a particular compound to be an enhancer or an inhibitor. The determination of occurrence or level of analytes according to alternatives a)-c) typically involves measurement of the enzymatic activity of the mammalian protein of the first aspect.

The terms "occurrence" and "level" comprise concentrations (quantitative), e.g. amount per unit volume, or relative amounts, such as relative to a reference substance that may be internal (i.e. is present together with the analyte in the sample) or external (i.e. is separate from the sample). An internal reference substance is typically added separately to the sample or the biological fluid, or is present already in the original biological material from which the analyte derives. The terms also include biological activity, for instance enzyme activity, if the compound is an enzyme active form of the mammalian protein as defined herein, for instance exhibiting phospholipase B activity and/or pro-phoshoplipase B activity. The terms also include presence or absence of the analyte (i.e. qualitative measurements).

The sample may be any kind of sample that may contain the mammalian protein and/or an entity related to the protein such as enhancer or an inhibitor of biological activity of the protein (see above). The sample typically derives from a biological fluid. Typical biological fluids encompass cell culture supernatants, tissue and tissue homogenates, blood and various blood fractions such as serum or plasma, lachrymal fluid, regurgitated fluid, urine, sweat, semen, cerebrospinal fluid, gastric juice, saliva, lymph, lung lavage fluid, intestinal fluid etc as well as various other liquid preparations containing a bio-organic compound, for instance various liquids obtained in various steps during the purification of the mammalian protein of the invention from its native sources (see the experimental part) or from its recombinant production.

In variants in which the capability of a particular compound to act as an inhibitor or enhancer is determined, the sample is typically the reaction mixture in which the compound is to interact with the mammalian protein of the invention. The sample is typically aqueous. It may be a liquid possibly containing insoluble material, or some kind of solid material, such as tissue, a gel, nitrocellulose sheet etc, that may contain a liquid part.

There are thus at least two main kinds of biological fluids: A) native biological fluids of a mammalian individual including also fluids derived from the native fluid by sample preparation, such as dilutions, fractions (plasma and serum from whole blood) etc, or B) process liquids obtained during production and/or isolation and/or enrichment of the mammalian protein from mammalian individuals or from recombinant processes generating the protein. If a sample is derived from a mammalian individual, the sample is typically taken for diagnostic purposes.

The terms "diagnosis", "diagnostic purposes" and the like in the context of the invention encompass the initial diagnostication of diseased conditions as well as the follow-up or monitoring of the diseased conditions after an actual diagnosis has been established, e.g. during a treatment or healing process or other kinds of observation periods (e.g. before the outbreak of the disease).

A first subaspect is a method for diagnosing a diseased condition associated with an abnormal level of the mammalian protein of the invention (analyte) in mammalian individuals (patients). The protein is typically a phospholipase B (PLB-II) or a pro-phospholipase B (pro-PLB-II). This subaspect comprises the steps of:

(i) measuring the level of the mammalian protein in a sample which is derived from a biological fluid originating from a mammalian individual, (ii) taking a found level that deviates from the level for normal (healthy) individuals of the same species, e.g. by being elevated, as an indication of said individual suffering from the diseased condition.

The level may be increased or decreased. Diseased conditions of interest typically relate to the biological activity of the mammalian protein of the invention, for instance its phospholipase activity or the ability of the subunits (SU1, SU2 etc) to exist as a multimeric protein or in fully or partly dissociated form. Increased levels are likely to be indicative of diseased conditions, such as i) an inflammatory disease/inflammation, ii) a microbial infection, such as a viral, bacterial or prion infection, iii) a cardiovascular disease, or iv) a lipid disorder, for instance involving neutrophil granulocytes and/or monocytes/macrophages.

Step (i) of the first subaspect may utilize

Alternative (a): one or more affinity counterparts specific for a native form of the mammalian protein described herein, for instance an antibody as defined for the second main aspect in an assay format as described for the second subaspect below, or Alternative (b): enzymic reactants, such as substrate, cofactors, enzyme activators etc, i.e. the method is an enzyme assay.

Other alternatives encompass chromatographic procedures that results in fractions in which the mammalian protein of the invention is enriched and thereafter measured.

A second subaspect is a biospecific affinity assay that utilizes an antibody preparation according to the second main aspect. This subaspect comprises the step of:

(i) contacting the sample with the antibody preparation specific for the mammalian protein described herein under conditions permitting formation of a complex between the antibody and the mammalian protein in an amount that is related to the level of the mammalian protein in the sample, (ii) measuring the level of the complex formed in step (i) and/or the level of the antibody not complexed to the protein, including the presence or absence of said complex, and (iii) calculating the level of the mammalian protein in the sample and/or in the biological fluid from which the sample derives from the level measured in step (ii).

The biological fluid is typically one of the main kinds discussed above (A and B).

If the sample and the biological fluid derive from a mammalian individual, the second subaspect may be performed for diagnostic purposes and will then comprise an extra step (iv) that will be the same as step (ii) of the first subaspect. In other words the second subaspect will then coincide with alternative (a) of the first subaspect.

The particular assay format to be used in the second subaspect is selected amongst those that are available for biospecific affinity assays. These formats as well as the principles for selection are well known in the field. They encompass that one or more affinity counterparts, for instance one or more antibody preparations specific for the analyte are used for the formation of an affinity complex, the level of which then is measured and related to the level of the analyte in the sample. The conditions are selected such that the level of the complex becomes a function of the level of analyte in the sample and in the biological fluid from which the sample derives. The formats may or may not use an affinity reactant that exhibits a label of the kinds discussed above for labelled forms of the mammalian protein of the invention (see first aspect of the invention), e.g. a labelled form of a) a mammalian protein of the first main aspect, or b) an antibody specific for this protein. During an assay, a labelled affinity reactant is typically incorporated into an affinity complex in an amount that is a function of a) the level of analyte in the sample, and/or b) the level of the complex formed that contains the mammalian protein and an antibody specific for the protein. The formats may or may not use an affinity reactant that is immobilized or immobilizable to a solid phase as described for the protein of the first main aspect. One way of grouping formats utilizing labelled reactants and/or immobilized or immobilizable reactants is into competitive and non-competitive assays. The sandwich format is a typical non-competitive format and utilizes as a rule at least two affinity counterparts that are specific for the mammalian protein (analyte) so that they simultaneously can bind to the analyte. One of these counterparts typically exhibits a label while the others exhibits another label or is immobilized or immobilizable to a solid phase. The competitive formats typically utilize an analyte analogue, i.e. the mammalian protein in labelled form or in immobilized or immobilizable form. The analogue is typically competing with the analyte for binding to a common affinity counterpart (e.g. antibody) that is in limiting amount. The affinity counterpart may be in labelled form in the case the analyte analogue is in immobilized or immobilizable form and in immobilized or immobilizable form if the analyte analogue is in labelled form. So called displacement assays are often considered as competitive formats. The formats may also be divided into heterogeneous and homogeneous formats where heterogeneous formats require a separation of labelled reactant incorporated in a complex from the same labelled reactant not incorporated in the complex before the measuring in step (ii) is carried out. The homogeneous formats do not require this kind of separation. Biospecific assay formats also include immunoblotting, agglutination formats (particles as labels), nephelometric/turbidometric formats etc.

The third subaspect comprises a) that the mammalian protein is enzyme active, for instance that it exhibits phospholipase B (PLB-II) activity or pro-phospholipase B (pro-PLB-II) activity, and b) that the activity level of either one or both of these entities is measured.

A first variant, the third subaspect comprises the steps of:
(i) incubating the sample containing the mammalian protein of the type described in the first main aspect with the appropriate substrate and other components necessary for substrate conversion,
(ii) measuring substrate conversion as a function of time, and
(iii) calculating the enzyme activity level of the mammalian protein in the sample and/or the biological fluid from which the sample derives based on the substrate conversion rate measured in step (ii).

It is important to secure that the sample is devoid of other enzymes that may cleave one or more of the acyl ester bonds (sn-1 and sn-2) that our novel phospholipase B does, for instance phospholipase A1, phospholipase A2, and other phospholipase Bs etc. This can be accomplished by removing such enzyme activities prior to step (i) or if the sample by definition is lacking such activities.

The sample typically derives from one of the two main kinds of biological fluids discussed above (A and B). If derived from a mammalian individual, the method may be performed for diagnostic purposes and the method carried out as part of the diagnostication of a diseased condition of the individual. The variant will then comprise a fourth step (iv) that will be the same as step (ii) in the first subaspect. In other word this variant then coincides with alternative (b) of the first subaspect.

A second variant of the third subaspect is a test for the capability of a compound (analyte) to promote or inhibit the transformation of a pro-phospholipase B (pro-PLB-II) of the invention to a phospholipase B (PLB-II) of the invention. In this variant the compound to be tested is the analyte and included in the incubation mixture of step (i). This variant thus comprises the steps of:
(i) bringing the pro-phospholipase B, a substrate for phospholipase B and the compound to be tested in contact with each other under activating conditions,
(ii) measuring conversion of the substrate as a function of time, and
(iii) determining from said conversion the capability of the test compound to promote or inhibit the activation of pro-phospholipase B to phospholipase B.

A third variant of the third subaspect is a method for testing the capability of a compound to inhibit or enhance the activity of a phospholipase B of the invention. In this variant the compound to be tested is the analyte and included into the incubation mixture of step (i). This third variant thus comprises the steps of:

(i) contacting phospholipase B of the invention with the compound to be tested and a substrate for phospholipase B with each other under conditions that allow substrate conversion,
(ii) measuring conversion of the substrate as a function of time, and
(iii) determining the enhancing or inhibiting capability of said compound from a comparison between the measured conversion in step (ii) and the conversion rate for selected standard conditions.

Both the second and the third variants of the third subaspect may be part of a drug development process in which the final drug is to be used for the treatment of a diseased condition that is related to natively occurring forms of a mammalian protein of the first aspect of the invention.

BEST MODES OF THE INVENTION

The best modes are:
1) Protein aspect: The human variants that are isolated and characterized in the experimental part. It is believed that in the future recombinant produced variants will become more important and therefore preferred. 2) Antibody aspect. The polyclonal antibody preparations used in the experimental part, in particular of specificities making them useful for biospecific assays of native forms of proteins of the first aspect in samples derived from biological fluids from humans. Important future variants will typically be monoclonal. 3) Method aspect: Biospecific assays for the native forms of the proteins defined in the first aspect and being present in samples derived from biological fluids of humans. Important future assays will typically be in the sandwich format and/or utilizing one or more antibody preparations that are monoclonal.

EXPERIMENTAL PART

Methods

Preparation of Granule Proteins. Granules were Isolated from the Buffy Coat of Normal human blood by a modification of the method described earlier (Peterson et al., *Eur. J. Haematol.* 40, 415-423 (1988)). The buffy coats, approximately 5 l originating from 100 healthy blood donors, were mixed with an equal volume of 2% Dextran T-500 in Phosphate-buffered saline (Dulbecco, without calcium and magnesium). The granulocyte-rich plasma was collected after sedimentation of the red cells for 1 h at room temperature. The granulocytes were washed twice in PBS and once in 0.34 M sucrose by centrifugation at 400 g for 10 min. The granulocyte pellet was resuspended in 5 volumes of 0.34 M sucrose. Isolated cells were then disrupted by nitrogen cavitation. Cell suspension was mixed with an equal volume of 0.34 M sucrose and the cells were pressurized at 4° C. for 30 min under nitrogen at 52 bar with constant stirring in a nitrogen bomb (Parr Instrument Company, Moline, Ill.). The cavitate was then collected into an equal volume of 0.34 M sucrose, 0.3 M NaCl and centrifuged for 20 min at 450 g at 4° C. The supernatant was centrifuged for 20 min at 10000 g at 4° C. to sediment the granules. After one cycle of freezing and thawing the granules were extracted with 5 volumes of 50 mM acetic acid for 1 h at 4° C. An equal volume of 0.4 M sodium acetate pH 4.0 was added and the extraction procedure was continued with magnetic stirring for 4 h at 4° C. The granule extract was then concentrated to approximately 5 ml using YM-2 filter (Amicon Corporation, Lexington, USA).

Chromatographic procedures. The procedure comprised four distinct steps (A-D) on three different columns:
Step A gel filtration: Acid extracts of granules obtained from human granulocytes were loaded on a Sephadex G-75 column (2.5×90 cm) and eluted by 0.2 M NaAc pH 4.5. The majority of the protein of the invention was contained in the second peak (elution volume/fractions 58-69 ml), as judged by SDS-PAGE after further separation of proteins in each pool on Mono-S column.
Step B ion-exchange chromatography: FPLC-system (Amersham Biosciences, Uppsala, Sweden) with a strong cationic exchanger Mono-S prepacked column Fractions/elution volumes of 58-69 ml from the gel filtration chromatography were applied to the Mono-S column pre-equilibrated with 0.1 M NaAc pH 4.0 and eluted by a linear gradient from 0 to 1.0 M NaCl in 0.1 M NaAc pH 4.0 (0.1-0.5 M NaCl for elution volume 6-27 ml and finally ending at 0.5 ml at elution volume 36 ml). The protein of the invention was eluted in the fractions/elution volume 19-22 ml (the second peak).
Step C ion exchange chromatography: The same system and column as in step B but the column was now equilibrated with 0.006 M sodium phosphate pH 7.4 and eluted by a linear gradient from 0.006 to 0.5 M sodium phosphate pH 7.4 for elution volumes 5-24 ml. The protein of the invention was eluted in the main second peak (fractions/elution volume 11-14 ml).
Step D hydroxy apatite chromatography: The fractions containing the protein of the invention from step C were applied to a hydroxyapatite column (BioRad) equilibrated with 0.02 M sodium phosphate buffer pH 7.2 and eluted with a linear gradient from 0.02 M sodium phosphate buffer pH 7.2 to 0.4 M sodium phosphate pH 6.8 for fractions/elution volumes 5-25 ml. Fractions/elution volumes 19-22 ml contained pure protein.

Approximately 0.5-20 µg of proteins from steps one to four of the purification were applied to SDS-PAGE, and proteins were visualized by silver staining.

The proteinase inhibitors, phenylmethylsulfonyl fluoride (PMSF) (100 mg/l) and Soybean trypsin inhibitor (SBTI) (100 mg/l) were added to all buffers from the cell disruption step to the first ion-exchange chromatography. Proteins in the chromatograms were measured by their absorbance at 280 nm. Ultrafiltration of pooled fractions was performed on a YM-10 filter. Buffer change was performed on PD-10 columns (Amersham Biosciences, Uppsala, Sweden).

Electrophoretic analysis. Proteins in aliquots of 0.5-20 µg were analyzed with sodium dodecylsulfate-polyacrylamide gel electrophoresis (SDS-PAGE) under reducing and non-reducing conditions using precast NuPAGE gel (Novex, Carlsbad, Calif.), according to manufacturer's instructions. Proteins were visualized by silver staining.
Amino Acid Analysis.

In-gel digestion and extraction. The 25 kDa and 45 kDa bands from one lane in a Coomassie stained gel were excised and minced into small pieces. The gel pieces were washed with distilled water, dehydrated with acetonitrile, and dried under vacuum. The sample was rehydrated and digested with a digestion buffer containing 50 mM $NH_4CO_3$, 5 mM $CaCl_2$ and 12.5 µg/ml of sequencing-grade modified trypsin (Promega, Madison, Wis.) over night at 37° C. The supernatant was collected, and the peptides were extracted from the gel pieces with 20 µl of 25 mM $NH_4HCO_3$ and several times with 20 µl of 50% acetonitrile/5% formic acid. Supernatants from each extraction were combined.

MALDI Mass Spectrometry. The tryptic digest was analysed by MALDI-Tof (Kompact MALDI 4, Kratos, UK). The mass analyser was scanned over a mass to charge ratio (m/z) range of 500 to 4000 amu and the resulting spectra were used for search of matching proteins in the NCBI database using the Mascot search program (Matrix Science).

Nanoelectrospray Mass Spectrometry (MS/MS). After the initial peptide scanning, one peptide was subjected to MS/MS analysis (Micro Q-Tof, Manchester, UK) followed by search with the fragmentation spectra in the NCBI data using search program Mascot (Matrix Science).

Protein determination. Protein concentration was determined with a Bio-Rad protein assay kit using bovine serum albumin as a standard by following the manufacturer's protocol.

Enzyme assay. The reaction mixture (40 µl final volume) contained 10 mM substrates, 100 mM phosphate buffer containing 3 mM of sodium azide ($NaN_3$) and 0.5% Triton X-100, pH 7.4, and 0.5 µg of enzyme or as indicated. Since the formation of the product (fatty acid) was linear with time for at least 24 h under the standard conditions, the reaction mixture was incubated for 18-20 h and the reaction was stopped by cooling on ice. Free fatty acid (FFA) was determined by means of the NEFA-C kit (WAKO chemicals, Neuss, Germany) according to the instructions of the manufacturer.

Positional specificity of the purified enzyme was determined using 1-palmitoyl-2-hydroxyl-phosphatidylcholine (1-palmitoyl-2-hydroxyl-PC) and 1-palmitoyl-2-[1-$^{14}$C] palmitoyl-phosphatidylcholine (1-palmitoyl-2-[1-$^{14}$C] palmitoyl-PC) as substrates. The hydrolyzing activity of the enzyme at the position of sn-1 acyl ester bonds of glycerophospholipids was determined as described above using 1-palmitoyl-2-hydroxyl-PC as substrate. For the hydrolyzing activity of the enzyme at the position of sn-2, Dipalmitoylphosphatidylcholine (Dipalmitoyl-PC (50 nm/reaction) was mixed with radiolabeled PC (1-palmitoyl-2-[1-$^{14}$C] palmitoyl-PC, 1×$10^5$ cpm/reaction). The mixture was dried out under nitrogen gas and resuspended in reaction buffer of 0.1 M sodium phosphate, 3 mM $NaN_3$ and 0.5% Triton X-100 at pH 7.4 by sonication to form micelles of phospholipids. The incubation was carried out at 37° C. for 20 h, the reaction was stopped by mixing with 0.8 ml Dole's reagent (32% isopropyl alcohol/67% heptane/1% 1M $H_2SO_4$, 20:5:1) and vortexed. After centrifugation 2 min at 1000 g, the upper phase containing free fatty acids was further purified by extraction with 50 mg silica gel suspended in heptane. Radiolabeled fatty acids were quantified by scintillation counting.

Experiment A: Didecanoyl-PC was incubated with the purified protein at different time of storage and free fatty acid release was measured. Enzymatic reactions were carried out with 0.5 µg of the purified protein for 20 h at 37° C.

Experiment B: Free fatty acid release from phospholipids, didecanoyl-PC (Dideca-PC), dipalmitoyl-PC (Dipalmi-PC), phosphatidylinositol (PI), phosphatidylethanolamine (PE) and lysophosphatidylcholine (Lyso-PC) was measured. Enzymatic reactions were carried out with 0.5 µg of the purified protein (stored at 4° C. for 15 w) for 18-20 h at 37° C.

Experiment C: The purified protein (stored at 4° C. for 16 w) was preincubated at room temperature or 37° C. for 15 min with released materials (0.5 µg) induced from neutrophils by PMA before incubation with Didecanoyl-PC. Enzymatic reactions were carried out with 0.5 µg of the protein for 20 h at 37° C. and free fatty acid release was measured.

Experiment D: Detection of phopholipase $A_2$ activity. Radioactive phospholipid, 1-palmitoyl-2-[1-$^{14}$C]palmitoyl-PC was incubated without (Control) or with 1 µg of the purified protein (stored at 4° C. 16 w) for 20 h at 37° C. and radioactivity was counted as described in the materials and methods section.

Analyses of the pH optimum, $K_m$ and $V_{max}$. The purified protein (0.5 µg) was added to tubes containing Didecanoyl-PC at varying pH (4.0-9.0). The Km and $V_{max}$ were calculated from Hanes plots of s/vi on Didecanoyl-PC concentration (s).

Preparative electrophoresis. Preparative gel electrophoresis was performed in the PrepCell system (Bio-Rad), following the instructions of the supplier. The acrylamide concentration of the cylindrical separation gel was 10%, and the gel was about 6 cm long. The stacking gel had an acrylamide concentration of 4% and was 2.5 cm long.

Antibody production. Laying hens were immunized with the purified protein. For the immunization 0.5 ml antigens in phosphate-buffered saline (PBS) were emulsified with an equal volume of Freund's adjuvant. The first immunization was performed with Freund's complete adjuvant and the booster immunization was with Freund's incomplete adjuvant. The amounts of antigen used for each immunization were 5 µg. White Leghorn hens were immunized intramuscularly in the breast muscle with the emulsified antigens. After the initial immunization, the animals received booster injections with 2-week intervals for three times and eggs were collected continuously after the initial immunization period of six weeks. Egg-yolk (2 ml) from individual eggs was mixed with 4 ml of 0.9% (w/v) NaCl, 5.25% (w/v) PEG 6000, 0.2% (w/v) $NaN_3$. After incubation overnight at 4° C., the mixture was centrifuged at 2000 g for 10 min. The clear supernatant was used for the detection of antibody response.

Cell Separation and Post Nuclear Supernatant Preparation

Blood cells were separated by density gradient centrifugation over isotonic 67% (v/v) of Percoll (Amersham Biosciences, Uppsala, Sweden). The interphase, containing the mononuclear cells and lymphocytes, was removed. The pellet fraction, containing erythrocytes and granulocytes, was treated for 15 min with ice-cold isotonic $NH_4Cl$ solution (155 mM $NH_4Cl$, 10 mM $KHCO_3$, 0.1 mM EDTA, pH 7.4) to lyse the erythrocytes, followed by hypotonic lysis of residual erythrocytes. The remaining granulocytes were washed twice in PBS (without $Ca^{2+}$). To further separate neutrophils from eosinophils, the isolated granulocytes were incubated for 1 h at 4° C. with anti-CD16 mAb-coated magnetic microbeads (at a proportion of 1×$10^7$ granulocytes in 30 µl PBS with 2% (v/v) newborn calf serum to 15 µl microbeads, Miltenyi Biotec, Bergisch Gladbach, Germany). The cells were subsequently allowed to pass through a steel matrix column in a magnetic field. Thereafter, the eosinophils that passed through were collected. The purity and viability of the eosinophils were ≧96 and 99%, respectively. After removing the magnetic field, the neutrophils were eluted with PBS. The purity of the neutrophils was more than 98%. Isolated eosinophils and neutrophils were resuspended respectively in 6% (w/v) of sucrose solution containing 10 µl/ml of protease inhibitor cocktail (Roche Diagnostics, Mannheim, Germany). Ultrasonication was performed to disrupt the eosinophils and neutrophils. Ultrasonicates were adjusted to 9% (w/v) of sucrose before centrifugation at 450 g for 20 min to eliminate the nuclei and intact cells. The post nuclear supernatants (25 µg) were loaded onto SDS-PAGE gels for immunoblotting. To obtain released materials, isolated neutrophils were resuspended in Hanks balanced salt solution at around 1×$10^8$ cells/ml and stimulated with PMA (4×$10^{-7}$ M) for 20 min at 37° C. After centrifugation the released material was aspirated. Under this condition, about 6% and 60% of primary and secondary granules were released from activated neutrophils, judged by the measurement of myeloperoxidase and human neutrophil lipocalin releases.

Immunoblotting. SDS-PAGE was performed under non-reducing conditions using precast NuPAGE gels (Novex, CA), according to manufacturer's instructions. For the immunoblotting, the proteins on the NuPAGE gel were transferred to a nitrocellulose membrane (0.2 μm), as described in the manufacturer's instructions. Additional binding sites were blocked by incubation of the nitrocellulose blot in 2% skim milk in 20 mM Tris-HCl, pH 7.4 for 1 h. The blot was incubated overnight with chicken antibodies against the fragment of 45 kDa diluted ¹/₁₀₀₀, followed by a 2 h incubation with peroxidase-conjugated rabbit anti-chicken Ig Y (Immuno-System, Uppsala). Color was developed with Immuno-Blot colorimetric assay kits (Bio-Rad, USA).

Results

Purification of a protein of the invention (putative phospholipase B=putative PLB) Approximately 0.5-20 μg of proteins from steps one to four of the purification were applied to SDS-PAGE, and proteins were visualized by silver staining. The purified protein from step four of the purification showed only two bands at molecular weights of 25 kDa and 45 kDa under both non-reducing and reducing conditions. However, these two molecules could not be separated by chromatographic means including Mono-P and the reversed phase chromatography. On gel filtration chromatography the purified native protein was eluted in one peak at a molecular weight of around 130 kDa, and on Mono-P chromatography the protein was eluted in one peak at a pH around 8.6.

Amino acid analyses. In order to identify the protein, the respective bands at 25 and 45 kDa on the SDS-PAGE were digested by trypsin, followed by MALDI-Tof and MS/MS analyses. The resulting spectrum was used to search for matching proteins in the NCBI database, using the Mascot search program. The search with the resulting spectrum from the bands at 25 kDa and 45 kDa yielded top scores of 76 and 116, respectively, for the hypothetical protein FLJ22662 with unknown function (a full-length protein of 63 kDa) (Protein scores greater than 67 are significant, $P<0.05$). The identified amino acid residues by MALDI-Tof and MS/MS are shown in Table 1. The residues from the 25 kDa band were found towards the N-terminus of the full length protein, while the residues from the 45 kDa band were found towards the C-terminus of the protein. It appears that the 25 and 45 kDa bands on the SDS-PAGE are fragments of the full-length hypothetical protein. Comparison of the hypothetical protein sequence with the GenBank sequence database by using the BLAST program revealed a number of similar proteins from mouse, rat and bovine with unknown functions, and a PLB from *Dictyostelium discoideum* (accession number Q8MWQ0). The amino acid sequence of the hypothetical protein has 32% identity with that of PLB from *Dictyostelium discoideum*.

Enzyme assays. To determine a possible deacylation activity of the putative PLB, freshly purified protein and materials from different steps of purification were incubated with either of several different substrates including didecanoyl-phosphatidylcholine (didecanoyl-PC), dipalmitoylphosphatidylcholine (dipalmitoyl-PC), phosphatidylinositol (PI), dipalmitoylphosphatidylethanolamine (PE) and 1-palmitoyl-2-hydroxylphosphatidylcholine (Lyso-PC). No activity was detected except for the acid extracts of granules. However, the purified protein stored at 4° C. for some period of time removed fatty acid from didecanoyl-PC, and the activity increased by storage time. In addition to phosphatidylcholine deacylation, the enzyme also showed deacylation activity on PI, PE and Lyso-PC. To investigate if a change in molecular weight was associated with the appearance of the deacylation activity, the purified protein stored at 4° C. for 16 weeks was analysed by SDS-PAGE. In addition to the major bands at 25 and 45 kDa, there appeared minor bands at molecular weights of around 21 and 41-44 kDa which partly shifted from the major bands, coinciding with the appearance of a significant deacylation activity. The more shifted from the major bands to the minor bands the more enzyme activity appeared. The enzyme is active at a broad pH range with an optimum of 7.4, when didecanoyl-PC was used as substrate and incubated at 37° C. From the Hanes plots a km of 1.1 mM and a $V_{max}$ value of 21.4 nM/min/mg were calculated when the protein (stored for 15 weeks) was used. It is obvious that the native purified protein needs molecular processing to acquire its activity. To investigate if activating factors are present in granules of neutrophils, the partly activated protein (0.5 μg, stored for 19 weeks) was pre-incubated with released materials (0.5 μg) induced by PMA from neutrophils for 15 min at room temperature and 37° C. before incubation with substrate mixture. The activity was increased about 10% by pre-incubation at room temperature and 30% by pre-incubation at 37° C.

Having known that the enzyme can remove fatty acid from the sn-1 position of 1-palmitoyl-2-hydroxyl-PC (Lyso-PC), it was incubated with labeled phosphatidylcholine, 1-palmitoyl-2-[1-$^{14}$C]palmitoyl-PC (GM Health care, Uppsala). The enzyme also removed fatty acid from the sn-2 position. Based on these results we conclude that we are dealing with a novel human PLB.

Antibody production and cellular localization of the novel PLB in neutrophils. By the time of immunization, the 25 kDa molecule was not identified as part of the hypothetical protein (FLJ22662), therefore, the 25 and 45 kDa molecules were separated by preparative electrophoresis and the antigens were separately injected to different chickens. The chicken given the 25 kDa molecule had no response to the antigen, while the chicken given the 45 kDa molecule had produced specific antibodies and reacted with the 45 kDa molecule as seen on an immunoblot. To investigate the origin of the protein in human granulocytes, neutrophil and eosinophil post nuclear supernatants were prepared and the proteins were separated on SDS-PAGE, followed by immunoblotting using the chicken anti-45 kDa antibodies. No band was detected in the post nuclear supernatant of eosinophils, but a band at a molecular weight of 45 kDa was detected in the post nuclear supernatant of neutrophils, indicating the neutrophil origin of the protein.

Discussion

This study has shown the identification, purification and characterization of a novel protein from acid extracts of granules of neutrophil granulocytes of healthy blood donors by means of a simple three-column procedure. The protein was identified as a novel PLB contained in the secretory granules of human neutrophils. The discovery sheds new light on the role of the neutrophil in inflammation, since this enzyme may not only have the capacity to kill bacteria but also have the capacity to generate lipid mediators of inflammation in local neutrophil involving processes.

PLBs are enzymes that can remove both the sn-1 and sn-2 fatty acids of glycerophospholipids, and thus displays both phospholipase $A_2$ and lysophospholipase activities. Several PLBs have been identified in bacteria (Farn et al., cited above), fungi (Ghannoun et al., cited above), *Dictyostelium discoideum* (Ferber et al., cited above), in mammalian cells (Gassama-Diagne et al., cited above; Tojo et al., cited above; Boll et al., cyed above; and Maury at al., cited above) and in bee and snake venoms. Genes coding for these PLBs were cloned and three distinct gene families have been identified from bacteria (Farn et al., cited above), fungi (Ghannoum et al., cited above) and mammals (Boll et al., cited above; Maury at al., cited above; Delagebeaudeuf et al., *J. Biol. Chem.* 273, 13407-13414 (1998); and Takemori et al., *J. Biol. Chem.* 273, 2222-2231 (1998)). However, the gene (FLJ22662) is not related to any of these gene families and the coded protein lacks the typical lipase motif (Schrag et al., cited above) found in lipases and phospholipases towards the C-terminus, suggesting that the putative PLB is a member of a new gene family of PLB as described for *Dictyostelium* PLB (Morgan et al., *Biochem. J.* 382, 441-449 (2004)). We suggest that this novel PLB should be named Human Phospholipase B type II (HPLB-II) to distinguish this gene product from the above mentioned PLBs. Since HPLB-II also displayed $PLA_2$ activity, it is fair to presume that it may be involved in diverse biological processes, such as arachidonic acid metabolism (Leslie C. C., *J. Biol. Chem.* 272, 16709-16712 (1997)), atherosclerosis (Webb et al., *Arterioscler. Thromb. Vasc. Biol.* 23, 263-268 (2003)) and antibacterial defence (Buckland et al., *Biochim. Biophys. Acta.* 1488, 71-82 (2000); and (Koduri et al., *J. Biol. Chem.* 277, 5849-5857 (2002)).

It was obvious that HPLB-II needs molecular processing to acquire its deacylation activity. Similar observation was made in guinea pig intestinal PLB, which is produced as a pro-enzyme activated upon shifting the molecular weight from 170 kDa to 140 kDa by trypsin treatment (Delagebeaudeuf et al., (1998) cited above). Materials from different steps of purification (step 2-4) showed no deacylation activity except for the acid extracts of granules. The activity seen in the acid extracts of granules was not likely due to $PLA_2$s present in neutrophil primary and secondary granules (Victor et al., *Febs Lett.* 136, 298-300 (1981); and Degousee et al., *J. Biol. Chem.* 277, 5061-5073 (2002)), because these are $Ca^{2+}$-dependent enzyme and $Ca^{2+}$ was not added to our incubation mixture. Therefore, there might be factors in the granules that lead to activation of the HPLB-II. This was confirmed by the pre-incubation of the partly activated enzyme with released materials from neutrophils. This pre-incubation further activated the enzyme. The mechanism, however, by which HPLB-II gains activity, remains to be investigated. Characterization of substrate specificity indicates that HPLB-II is not limited to hydrolyzing phosphatidyl-PC, as PI and PE also serve as substrates. The enzyme is active at a broad pH range with an optimum of 7.4, suggesting an extracellular deacylation role. The immunoblotting was chosen to determine the localization of HPLB-II in human granulocytes, because the antigen used for immunization was in a denatured form after separation by preparative electrophoresis. Therefore, the antibodies raised in this study are suitable to detect the denatured form of the molecule. The immunoblotting indicated a neutrophil origin of HPLB-II. However, the immunoblotting failed to show a band at a molecular weight of 63 kDa (a molecular weight of full length hypothetical protein FLJ22662). The explanation for this could be that the full length protein of 63 kDa is cleaved by proteases present in the preparation of the post nuclear supernatant. However, we find this unlikely, since a protease inhibitor cocktail was included in the preparation. Another explanation is that the full length protein already has been processed into fragments of 25 and 45 kDa during granulopoiesis.

The fragments 25 and 45 kDa were seen on SDS-PAGE under both reducing and non-reducing conditions. However, the two molecules were not separated by chromatographic procedures applied in this study including chromatofocusing and reversed phase chromatography. These findings and the apparent molecular weight of 130 kDa by gel filtration suggest that the protein in fact is an oligomeric protein comprising at least two 25 kDa and two 45 kDa molecules associated non-covalently.

TABLE 1

Peptide mass fingerprint of the purified protein

| 25 kDa subunit | | | 45 kDa subunit | | |
|---|---|---|---|---|---|
| No | m/z | Residues no in FLJ22662 | No | m/z | Residues no in FLJ22662 |
| 1 | 1129.62 | 47-57 | 1 | 2685.34 | 233-255 |
| 2 | 1160.62 | 52-61 | 2 | 1819.85 | 259-273 |
| 3 | 1144.62 | 75-84 | 3 | 1468.80 | 313-324 |
| 4 | 895.41 | 134-140 | 4 | 1921.89 | 345-360 |
| 5 | 832.42 | 141-146 | 5 | 2715.36 | 371-393 |
| 6 | 1230.57 | 151-159 | 6 | 1750.85 | 394-407 |
| 7 | 810.37 | 154-159 | 7 | 1622.75 | 395-407 |
| 8 | 1821.91 | 160-176 | 8 | 1381.69 | 421-432 |
| | | | 9 | 1251.48 | 466-475 |
| | | | 10 | 2972.53 | 493-520 |
| | | | 11 | 2595.32 | 527-548 |

The amino acid sequences/fragments shown in bold were determined by MS/MS

Quantitation of the Innovative Protein in Various Biological Fluids.

A double antibody radioimmunoassay (RIA) was developed for the measurement of HPLB-II. HPLB-II was labeled with $^{125}I$ by the chloramine-T method. Free $^{125}I$ was separated from labeled protein by gel filtration on a Sephadex G-25 column. Before RIA incubation, the labeled antigen was diluted in assay buffer (50 mM sodium phosphate, pH 7.4, containing 80 mM NaCl, 10 Mm Na-EDTA, 0.2% Bovine serum albumin, 0.02% $NaN_3$ 0.2% CTAB and 0.5% Tween 20) to 38000±2000 cpm/100 µl (tracer). A 50 µl solution of either sample or standard (2-128 µl/l) was sequentially mixed with 50 µl of labeled HPLB-II (tracer), 50 µl of specific antibodies raised in rabbit (diluted 1:60000 in assay buffer) and incubated for 3 h at room temperature. Thereafter, 0.5 ml of decanting suspension containing Sephadex anti-rabbit IgG raised in sheep were added and the incubation continued for 1 h at 4° C. HPLB-II-antibody complexes bound on Sephadex anti-rabbit IgG were separated and pelleted by centrifugation at 18° C. for 15 min at 4000 rpm. After decantation, the radioactivity was measured in a gamma counter.

Results: A standard curve indicating a possible measuring range 1-100 µg/L of PLB-II (four subunits) with a limit of detection of 1 µg/L. PLB-II in normal serum was undetectable whereas raised levels were found in serum obtained from patients with acute bacterial infections (3-9 µg/L). Highly raised levels were also found in lung lavage fluids of patients with chronic obstructive pulmonary disease (1-21 µg/L) and intestinal fluid of patients with inflammatory bowel disease (22-52 µg/L).

Certain innovative aspects of the invention are defined in more detail in the appending claims. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. An isolated mammalian protein, comprising at least one SU1 subunit comprising SEQ ID NO: 2, the SU1 subunit having a molecular weight within the range of 15-35 kDa, and/or at least one SU2 subunit comprising SEQ ID NO: 3, the SU2 subunit having a molecular weight within the range of 30-60 kDa.

2. The mammalian protein of claim 1, comprising an SU1 subunit and devoid of an SU2 subunit.

3. The mammalian protein of claim 1, comprising an SU2 subunit and devoid of an SU1 subunit.

4. The mammalian protein of claim 1, comprising at least one SU1 subunit and at least one SU2 subunit, wherein the SU1 subunit and the SU2 subunit are derived from the same mammalian species.

5. The mammalian protein of claim 1, having a molecular weight within the range of 15-240 kDa.

6. The mammalian protein of claim 1, wherein the protein includes at least one SU2 subunit of SEQ ID NO: 3 and is a pro-phospholipase B (PLB-II).

7. The mammalian protein of claim 6, wherein the protein is devoid of the SU1 subunit.

8. A protein comprising an activated form of the mammalian protein of claim 6, wherein the protein exhibits phospholipase B activity and comprises the SU2 subunit in activated form with a molecular weight that is at least 0.5 kDa lower than in an inactive native form of the SU2 subunit.

9. The protein of claim 8, wherein the protein is devoid of the SU1 subunit.

10. The mammalian protein of claim 1, wherein the protein is devoid of a lipase consensus motif of five amino acid residues having glycine at both end positions and serine in the middle position.

11. The mammalian protein of claim 1, wherein the protein is labelled with an analytically detectable tag, is immobilized to a solid phase, or is equipped with an immobilizing tag that renders the mammalian protein immobilizable to a solid phase.

12. An antibody which is specifically directed against the mammalian protein of claim 1, obtained by immunization with said mammalian protein, or a recombinantly produced form of an antibody produced by immunization with said mammalian protein.

13. A method for determining the occurrence or level of the mammalian protein of claim 1 in a sample, comprising contacting the sample with an antibody specifically directed against the mammalian protein, and determining the presence or amount of protein-antibody conjugate.

14. The method of claim 13, for diagnosing a disease condition associated with an abnormal level of the mammalian protein in a mammalian patient and selected from the group consisting of bacterial infection, chronic obstructive pulmonary disease, and inflammatory bowel disease, wherein the method further comprises comparing the determined amount of conjugate with an amount of conjugate representative of healthy individuals of the same species, wherein a determined amount that deviates from the amount representative of healthy individuals of the same species is an indication that said patient suffers from the disease condition.

15. An antibody which is specifically directed against the mammalian protein of claim 2, obtained by immunization with said mammalian protein, or a recombinantly produced form of an antibody produced by immunization with said mammalian protein.

16. An antibody which is specifically directed against the mammalian protein of claim 3, obtained by immunization with said mammalian protein, or a recombinantly produced form of an antibody produced by immunization with said mammalian protein.

17. An antibody which is specifically directed against the mammalian protein of claim 6.

18. An antibody which is specifically directed against the mammalian protein of claim 8.

19. The mammalian protein of claim 1, comprising two SU1 subunits and two SU2 subunits.

20. An antibody which is specifically directed against the mammalian protein of claim 19.

21. The mammalian protein of claim 19, wherein the SU1 subunits are of 25 kDa molecular weight and the SU2 subunits are of 45 kDa molecular weight.

22. An antibody which is specifically directed against the mammalian protein of claim 21.

23. A method for determining the occurrence or level of the mammalian protein of claim 19 in a sample, comprising contacting the sample with an antibody specifically directed against the mammalian protein, and determining the presence or amount of protein-antibody conjugate.

24. The method of claim 23, for diagnosing a disease condition associated with an abnormal level of the mammalian protein in a mammalian patient and selected from the group consisting of bacterial infection, chronic obstructive pulmonary disease, and inflammatory bowel disease, wherein the method further comprises comparing the determined amount of conjugate with an amount of conjugate representative of healthy individuals of the same species, wherein a determined amount that deviates from the amount representative of healthy individuals of the same species is an indication that said patient suffers from the disease condition.

25. A method for determining the occurrence or level of the mammalian protein of claim 6 in a sample, comprising contacting the sample with an antibody specifically directed against the mammalian protein, and determining the presence or amount of protein-antibody conjugate.

26. The method of claim 25, for diagnosing a disease condition associated with an abnormal level of the mammalian protein in a mammalian patient and selected from the group consisting of bacterial infection, chronic obstructive pulmonary disease, and inflammatory bowel disease, wherein the method further comprises comparing the determined amount of conjugate with an amount of conjugate representative of healthy individuals of the same species, wherein a determined amount that deviates from the amount representative of healthy individuals of the same species is an indication that said patient suffers from the disease condition.

27. The antibody of claim 12, wherein the antibody is a monoclonal antibody.

28. The antibody of claim 12, wherein the antibody is a polyclonal antibody.

29. The antibody of claim 15, wherein the antibody is a monoclonal antibody.

30. The antibody of claim 15, wherein the antibody is a polyclonal antibody.

31. The antibody of claim 16, wherein the antibody is a monoclonal antibody.

32. The antibody of claim 16, wherein the antibody is a polyclonal antibody.

33. The antibody of claim 17, wherein the antibody is a monoclonal antibody.

34. The antibody of claim 17, wherein the antibody is a polyclonal antibody.

35. The antibody of claim 22, wherein the antibody is a monoclonal antibody.

36. The antibody of claim 22, wherein the antibody is a polyclonal antibody.

* * * * *

SEQUENCE LISTING

<160> NUMBER OF SEQ ID NOS: 3

<210> SEQ ID NO 1
<211> LENGTH: 552
<212> TYPE: PRT
<213> ORGANISM: Homo sapiens

<400> SEQUENCE: 1

```
Met Thr Arg Gly Gly Pro Gly Gly Arg Pro Gly Leu Pro Gln Pro Pro
  1               5                  10                  15

Pro Leu Leu Leu Leu Leu Leu Pro Leu Leu Val Thr Ala Glu
                 20                  25                  30

Pro Pro Lys Pro Ala Gly Val Tyr Tyr Ala Thr Ala Tyr Trp Met Pro
             35                  40                  45

Ala Glu Lys Thr Val Gln Val Lys Asn Val Met Asp Lys Asn Gly Asp
 50                  55                  60

Ala Tyr Gly Phe Tyr Asn Asn Ser Val Lys Thr Thr Gly Trp Gly Ile
 65                  70                  75                  80

Leu Glu Ile Arg Ala Gly Tyr Gly Ser Gln Thr Leu Ser Asn Glu Ile
                 85                  90                  95

Ile Met Phe Val Ala Gly Phe Leu Glu Gly Tyr Leu Thr Ala Pro His
                100                 105                 110

Met Asn Asp His Tyr Thr Asn Leu Tyr Pro Gln Leu Ile Thr Lys Pro
            115                 120                 125

Ser Ile Met Asp Lys Val Gln Asp Phe Met Glu Lys Gln Asp Lys Trp
        130                 135                 140

Thr Arg Lys Asn Ile Lys Glu Tyr Lys Thr Asp Ser Phe Trp Arg His
145                 150                 155                 160

Thr Gly Tyr Val Met Ala Gln Ile Asp Gly Leu Tyr Val Gly Ala Lys
                165                 170                 175

Lys Arg Ala Ile Leu Glu Gly Thr Lys Pro Met Thr Leu Phe Gln Ile
            180                 185                 190

Gln Phe Leu Asn Ser Val Gly Asp Leu Leu Asp Leu Ile Pro Ser Leu
        195                 200                 205

Ser Pro Thr Lys Asn Gly Ser Leu Lys Val Phe Lys Arg Trp Asp Met
    210                 215                 220

Gly His Cys Ser Ala Leu Ile Lys Val Leu Pro Gly Phe Glu Asn Ile
225                 230                 235                 240

Leu Phe Ala His Ser Ser Trp Tyr Thr Tyr Ala Ala Met Leu Arg Ile
                245                 250                 255

Tyr Lys His Trp Asp Phe Asn Ile Ile Asp Lys Asp Thr Ser Ser Ser
            260                 265                 270

Arg Leu Ser Phe Ser Ser Tyr Pro Gly Phe Leu Glu Ser Leu Asp Asp
        275                 280                 285

Phe Tyr Ile Leu Ser Ser Gly Leu Ile Leu Leu Gln Thr Thr Asn Ser
    290                 295                 300

Val Phe Asn Lys Thr Leu Leu Lys Gln Val Ile Pro Glu Thr Leu Leu
305                 310                 315                 320

Ser Trp Gln Arg Val Arg Val Ala Asn Met Met Ala Asp Ser Gly Lys
                325                 330                 335

Arg Trp Ala Asp Ile Phe Ser Lys Tyr Asn Ser Gly Thr Tyr Asn Asn
            340                 345                 350

Gln Tyr Met Val Leu Asp Leu Lys Lys Val Lys Leu Asn His Ser Leu
        355                 360                 365
```

```
Asp Lys Gly Thr Leu Tyr Ile Val Glu Gln Ile Pro Thr Tyr Val Glu
    370                 375                 380

Tyr Ser Glu Gln Thr Asp Val Leu Arg Lys Gly Tyr Trp Pro Ser Tyr
385                 390                 395                 400

Asn Val Pro Phe His Glu Lys Ile Tyr Asn Trp Ser Gly Tyr Pro Leu
                405                 410                 415

Leu Val Gln Lys Leu Gly Leu Asp Tyr Ser Tyr Asp Leu Ala Pro Arg
            420                 425                 430

Ala Lys Ile Phe Arg Arg Asp Gln Gly Lys Val Thr Asp Thr Ala Ser
            435                 440                 445

Met Lys Tyr Ile Met Arg Tyr Asn Asn Tyr Lys Lys Asp Pro Tyr Ser
    450                 455                 460

Arg Gly Asp Pro Cys Asn Thr Ile Cys Cys Arg Glu Asp Leu Asn Ser
465                 470                 475                 480

Pro Asn Pro Ser Pro Gly Gly Cys Tyr Asp Thr Lys Val Ala Asp Ile
                485                 490                 495

Tyr Leu Ala Ser Gln Tyr Thr Ser Tyr Ala Ile Ser Gly Pro Thr Val
            500                 505                 510

Gln Gly Gly Leu Pro Val Phe Arg Trp Asp Arg Phe Asn Lys Thr Leu
            515                 520                 525

His Gln Gly Met Ala Glu Val Tyr Asn Phe Asp Phe Ile Thr Met Lys
    530                 535                 540

Pro Ile Leu Lys Leu Asp Ile Lys
545                 550

<210> SEQ ID NO 2
<211> LENGTH: 130
<212> TYPE: PRT
<213> ORGANISM: Homo sapiens

<400> SEQUENCE: 2

Met Pro Ala Glu Lys Thr Val Gln Val Lys Asn Val Met Asp Lys Asn
1               5                   10                  15

Gly Asp Ala Tyr Gly Phe Tyr Asn Asn Ser Val Lys Thr Thr Gly Trp
            20                  25                  30

Gly Ile Leu Glu Ile Arg Ala Gly Tyr Gly Ser Gln Thr Leu Ser Asn
        35                  40                  45

Glu Ile Ile Met Phe Val Ala Gly Phe Leu Glu Gly Tyr Leu Thr Ala
    50                  55                  60

Pro His Met Asn Asp His Tyr Thr Asn Leu Tyr Pro Gln Leu Ile Thr
65                  70                  75                  80

Lys Pro Ser Ile Met Asp Lys Val Gln Asp Phe Met Glu Lys Gln Asp
                85                  90                  95

Lys Trp Thr Arg Lys Asn Ile Lys Glu Tyr Lys Thr Asp Ser Phe Trp
            100                 105                 110

Arg His Thr Gly Tyr Val Met Ala Gln Ile Asp Gly Leu Tyr Val Gly
        115                 120                 125

Ala Lys
    130

<210> SEQ ID NO 3
<211> LENGTH: 316
<212> TYPE: PRT
<213> ORGANISM: Homo sapiens

<400> SEQUENCE: 3
```

-continued

```
Val Leu Pro Gly Phe Glu Asn Ile Leu Phe Ala His Ser Ser Trp Tyr
1               5                   10                  15

Thr Tyr Ala Ala Met Leu Arg Ile Tyr Lys His Trp Asp Phe Asn Ile
            20                  25                  30

Ile Asp Lys Asp Thr Ser Ser Arg Leu Ser Phe Ser Ser Tyr Pro
        35                  40                  45

Gly Phe Leu Glu Ser Leu Asp Asp Phe Tyr Ile Leu Ser Ser Gly Leu
        50                  55                  60

Ile Leu Leu Gln Thr Thr Asn Ser Val Phe Asn Lys Thr Leu Leu Lys
65              70                  75                      80

Gln Val Ile Pro Glu Thr Leu Leu Ser Trp Gln Arg Val Arg Val Ala
            85                  90                  95

Asn Met Met Ala Asp Ser Gly Lys Arg Trp Ala Asp Ile Phe Ser Lys
            100                 105                 110

Tyr Asn Ser Gly Thr Tyr Asn Asn Gln Tyr Met Val Leu Asp Leu Lys
            115                 120                 125

Lys Val Lys Leu Asn His Ser Leu Asp Lys Gly Thr Leu Tyr Ile Val
        130                 135                 140

Glu Gln Ile Pro Thr Tyr Val Glu Tyr Ser Glu Gln Thr Asp Val Leu
145                 150                 155                 160

Arg Lys Gly Tyr Trp Pro Ser Tyr Asn Val Pro Phe His Glu Lys Ile
                165                 170                 175

Tyr Asn Trp Ser Gly Tyr Pro Leu Leu Val Gln Lys Leu Gly Leu Asp
            180                 185                 190

Tyr Ser Tyr Asp Leu Ala Pro Arg Ala Lys Ile Phe Arg Arg Asp Gln
        195                 200                 205

Gly Lys Val Thr Asp Thr Ala Ser Met Lys Tyr Ile Met Arg Tyr Asn
210                 215                 220

Asn Tyr Lys Lys Asp Pro Tyr Ser Arg Gly Asp Pro Cys Asn Thr Ile
225                 230                 235                 240

Cys Cys Arg Glu Asp Leu Asn Ser Pro Asn Pro Ser Pro Gly Gly Cys
            245                 250                 255

Tyr Asp Thr Lys Val Ala Asp Ile Tyr Leu Ala Ser Gln Tyr Thr Ser
        260                 265                 270

Tyr Ala Ile Ser Gly Pro Thr Val Gln Gly Gly Leu Pro Val Phe Arg
        275                 280                 285

Trp Asp Arg Phe Asn Lys Thr Leu His Gln Gly Met Ala Glu Val Tyr
290                 295                 300

Asn Phe Asp Phe Ile Thr Met Lys Pro Ile Leu Lys
                305                 310                 315
```